(12) United States Patent
Bamberger et al.

(10) Patent No.: US 6,555,323 B2
(45) Date of Patent: Apr. 29, 2003

(54) ASSAY FOR ABCA1

(75) Inventors: Mark J. Bamberger, South Glastonbury, CT (US); Omar L. Francone, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/761,890

(22) Filed: Jan. 17, 2001

(65) Prior Publication Data

US 2002/0061511 A1 May 23, 2002

Related U.S. Application Data

(60) Provisional application No. 60/180,943, filed on Feb. 8, 2000.

(51) Int. Cl.$^7$ .............................................. G01N 33/53
(52) U.S. Cl. ...................... 435/7.1; 435/7.2; 435/7.21; 435/4; 435/6
(58) Field of Search .................. 435/4, 7.1, 7.2, 435/7.21, 11.6

(56) References Cited

PUBLICATIONS

Higgins, *Annu. Rev. Cell Biol.*, 8:67–113 (1992).
Ames et al., *FASEB J.*, 6:2660–66 (1992).
Higgins, *CEll*, 82:693–96 (1995).
Gottesman et al., *Annu. Rev. Biochem.*, 62:385–428 (1992).
Thomas et al., *Science*, 268:426–29 (1995).
Riordan et al., *Science*, 245:1066–73 (1989).
Hanrahan et al., in *Ion Channels and Genetic Diseases* ( Dawson, D. C. & Frizzell, R. A., Eds.) vol. 50, pp. 125–137, Society of General Physiologists Symposium Series, Rockefeller University Press, New York (1995).
Sarkadi et al., *J. Biol. Chem.*, 267:4854–58 (1992).
Shapiro et al., *J. Biol. Chem.*, 269:3745–54 (1994).
Ko et al., *J. Biol. Chem.*, 270:22093–96 (1995).
Doige et al., *Biochim. Biophys. Acta*, 1109:149–60 (1992).
Müller et al., *J. Biol. Chem.*, 271:1877–83 (1996).
Beaudet et al., *J. Biol. Chem.*, 270:17159–70 (1995).
Baukrowitz et al., *Neuron*, 12:473–82 (1994).
Carson et al., *J. Biol. Chem.*, 270:1711–17 (1995).
Gunderson et al., *Cell*, 82:231–39 (1995).
Smit et al., *PNAS*, 90:9963–67 (1993).
Picciotto et al., *J. Biol. Chem.* 267:12742–52 (1992).
Gill et al., *Cell*, 71:23–32 (1992).
Hardy et al., *EMBO J.*, 14:68–75 (1995).
Walker et al., *EMBO J.*, 1:945–51 (1982).
Saraste et al., *Trends Biochem. Sci.*, 15:430–34 (1990).
Miler et al., *Lancet*, 1:965–68 (1977).
Keys, *Lancet*, 2:603–06 (1980).
Shaefer, *Arteriosclerosis*, 4:303–22 (1984).
Glomset, *J. Lipid Res.*, 9:155–67 (1968).
Fielding et al., *J. Lipid Res.*, 38:1503–21 (1997).
Oram et al., *J. Lipid Res.*, 37:2743–91 (1996).
Mendez, *J. Lipid Res.*, 38:1807–21 (1997).
Remaley et al., *Arterioscler. Thromb. Vasc. Biol.*, 17:1813–21 (1997).
Mendez et al., *J. Lipid Res.*, 37:2510–24 (1996).
Fredrickson, *J. Clin. Invest.*, 43:228–36 (1964).
Assmann et al., in *The Metabolic Basis of Inherited Disease*, pp. 2053–72, Scriver et al., Eds., McGraw–Hill, New York, NY (1995).
Serfaty–Lacrosniere et al., *Atherosclerosis*, 107:85–98 (1994).
Francis et al., *J. Clin. Invest.*, 96:78–87 (1995).
Rogler et al., *Arterioscler. Thromb. Vasc. Biol.*, 15:683–90 (1995).
Walter et al., *Biochem. Biophys. Res. Comm.*, 205:850–56 (1994).
Horowitz et al., *J. Clin. Invest.*, 91:1743–52 (1993).
Rothblat et al., *J. Lipid Res.*, 40:781–96 (1999).
Lawn et al., *J. Clin. Invest.*, 104(8):R25–R31 (1999).
Brooks–Wilson et al., *Nature Genetics*, 22:336–45 (1999).
Bodzioch et al., *Nature Genetics*, 22:347–51 (1999).
Rust et al., *Nature Genetics*, 22:352–55 (1999).
Luciani et al., *Genomics*, 21:150–59 (1994).
Becq et al., J. Biol. Chem., 272:2695–99 (1997).
Langmann et al., Biochem. Biophys. Res. Comm., 257:29–33 (1999).
Collet et al., Biochem. Biophys. Res. Comm., 258:73–76 (1999).
Young et al., *Nature Genetics*, 22:316–18 (1999).

*Primary Examiner*—Sheela Huff
(74) *Attorney, Agent, or Firm*—Peter C. Richardson; Gregg C. Benson; Gregory P. Raymer

(57) ABSTRACT

This invention relates to novel methods of measuring the activity and/or levels of ABCA1 protein, including the use of acceptors of ABCA1 substrates, as well as methods involving the measurement of ABCA1 mRNA and protein levels.

15 Claims, No Drawings

ASSAY FOR ABCA1

CROSS REFERENCE TO RELATED APPLICATION

This application claims priority of U.S. provisional application No. 60/180,943, filed Feb. 8, 2000.

BACKGROUND OF THE INVENTION

ABCA transporters, the largest and most diverse family of transport proteins, are associated with many important biological processes, as well as with clinical problems such as cystic fibrosis, antigen presentation, and multidrug resistance of cancers. The designation ABCA transporters recognizes a highly conserved ATP-binding cassette, which is the most characteristic feature of this super family. Typically, ABCA transporters utilize the energy of ATP hydrolysis to pump substrate across the membrane against a concentration gradient. Each ABCA transporter is relatively specific for a given substrate. Nevertheless, the variety of substrates handled by different transporters is enormous: ABCA transporters specific for amino acids, sugars, inorganic ions, polysaccharides, peptides, and even proteins have been characterized (1).

ABCA1 transporters are implicated in the vectorial movement of a wide variety of substrates across biological membranes (2,3). Most of the mammalianABCA transporters identified so far have been associated with clinically relevant phenotypes (3). Human P-glycoprotein confers resistance to chemotherapeutic drugs on tumor cells (4). Persistent hyperinsulinemic hypoglycemia of infancy is associated with mutation of SUR, the receptor for sulfonylureas (5). Cystic fibrosis is caused by mutations in the gene encoding the cystic fibrosis transmembrane conductance regulator (CFTR), a cAMP-dependent chloride channel (6,7).

The basic structural unit of an ABCA transporter consists of a pair of nucleotide binding folds (NBF) and two transmembrane domains, each composed typically of six transmembrane spanners (2,3). Their activity as transporters is dependent on their interaction with ATP at the NBFs followed by its hydrolysis (8–17), and in some cases evidence has been provided for a further regulation via phosphorylation of serine/threonine residues in the region linking the two symmetric halves (7, 18–20). The NBF domains contain the highly conserved phosphate binding loop (21) that forms intimate contacts with the β- and γ-phosphates of bound ATP (22) and an additional diagnostic motif, the active transport signature, whose function is so far unknown. The above description is not fully applicable to the newly discovered ½-transporters, though much is analogous.

Low serum HDL cholesterol (HDL-C) concentrations have been identified as a good predictor for coronary artery disease (23,24). A variety of factors contribute to low HDL-C levels including genes harboring a basic defect, modifying genes, and environmental factors (25). Low HDL syndromes are genotypically heterogeneous and understanding their molecular basis could explain the essential role of HDL in plasma cholesterol homeostasis and atherosclerosis.

A major cardioprotective activity of HDL is ascribed to its role in reverse cholesterol transport, which is the flux of cholesterol from peripheral cells such as tissue macrophages, through plasma lipoproteins to the liver, where it can be excreted in the form of bile salts (26). Lipid-poor particles, particularly those containing the major HDL protein, apoA-I, play a major role in this process (27,28). They interact with the cell surface to remove excess cholesterol and phospholipids by an active transport pathway involving the Golgi apparatus (28–31). Although the cellular proteins remain to be identified, recent studies have shown that this pathway is severely impaired in subjects with homozygous Tangiers disease (TD).

TD is a rare genetic disorder that is characterized by near or complete absence of circulating HDL and by the accumulation of cholesteryl esters in many tissues, including tonsils, lymph nodes, liver, spleen, thymus, intestine, and Schwann cells (32,33). Most patients were initially identified by enlarged yellow-orange tonsils and symptoms of neuropathy (33). In addition to zero or near zero plasma levels of HDL, patients with TD have a roughly 50% reduction in LDL and a moderate elevation in triglycerides. Although low levels of HDL represent a clear predictor of premature coronary artery disease, the presence of increased cardiovascular disease in patients with TD was at first unclear, as concomitant reduction in LDL may offer some protection from coronary artery disease. However, a review of 54 cases of homozygous TD revealed a 4- to 6-fold increase in cardiovascular disease compared with controls, depending on the age group considered (34).

Cells from subjects with TD are defective in the process of apolipoprotein-mediated removal of cholesterol and phospholipids (30, 35–37). Thus, it is likely that the severe HDL deficiency in TD stems from the inability of nascentapoA-I to acquire lipids. Because they do not mature into lipid-rich HDL, the nascent lipoproteins in these patients are rapidly removed from the plasma, resulting in near zero levels of circulating HDL and apoA-I (38). Although some cell types can rid themselves of substantial amounts of excess cholesterol by other means such as aqueous diffusion (39), a defect in the pathway of apolipoprotein-mediated efflux is likely to be at the root of the massive tissue deposition of sterols and the pathology observed in patients with TD (40).

Using linkage analysis and positional cloning, three separate groups identified mutations in the human ABCA1 gene that are linked to Tangiers disease (41–43). ABCA1 possesses all the distinguishing features of other ATP-binding proteins, including two ATP-binding segments and two transmembrane domains (44). ABCA1 is a 220-kDa glycoprotein expressed by macrophages and required for engulfment of cells undergoing programmed cell death (45). Additionally, ABCA1 has been found in numerous other cells types (46). ABCA1 is activated by protein kinases (45) and is modulated at the transcriptional level by increased cellular cholesterol stores (47). Recently, ABCA1 has been associated with the initial steps of reverse cholesterol transport from cells (48). In addition, ABCA1 may have critically important functions in the body by virtue of its ability to function as a cholesterol gatekeeper.

According to Becq et al. (45), ABCA1 generates an anion flux sensitive to glibenclamide, sulfobromophthalein, and blockers of anion transporters. The anion flux generated by ABCA1 is up-regulated by orthovanadate, cAMP, protein kinase A, okadaic acid, and other compounds. In other ABCA transporters, mutating the conserved lysine in the nucleotide binding folds was found to severely reduce or abolish hydrolysis of ATP, which in turn altered the activity of the transporter. In ABCA1, replacement of the conserved lysine 1892 in the Walker A motif of the second nucleotide binding fold increased the basal ionic flux, did not alter the pharmacological inhibitory profile, but abolished the response to orthovanadate and cAMP agonists. Therefore, it was concluded that ABCA1 is a cAMP-dependent and sulfonylurea-sensitive anion transporter (45).

SUMMARY OF THE INVENTION

In a first aspect, the present invention relates to a method of determining the ability of a test compound to affect the activity of ABCA1 protein, said method comprising the steps of introducing labeled substrate into ABCA1-expressing cells, adding a test composition comprising said test compound to a first portion of said cells, and adding a control composition to a second portion of said cells, wherein said control composition is essentially identical to said test composition except that said control composition does not include said test compound, and comparing the level of efflux of substrate from said first portion of said cells to the level of efflux of substrate from said second portion of said cells, wherein a change in the level of efflux indicates that said test compound affects the activity of the ABCA1 protein.

In a preferred embodiment of the first aspect, a positive control composition is added to a third portion of said cells, said positive control composition being essentially identical to said control composition except that said positive control composition comprises an ABCA1 agonist, and wherein the level of efflux of substrate from said third portion of said cells is compared to the levels of efflux of substrate from said first and said second portions of said cells.

In another preferred embodiment of the first aspect, a negative control composition is added to a third portion of said cells, said negative control composition being essentially identical to said control composition except that said negative control composition comprises an ABCA1 antagonist, and wherein the level of efflux of substrate from said third portion of said cells is compared to the levels of efflux of substrate from said first and said second portions of said cells.

In yet another preferred embodiment of the first aspect, the level of efflux of substrate from each portion of said cells is measured prior to said comparing step.

In yet another preferred embodiment of the first aspect, the level of efflux of substrate from each portion of said cells is measured by separately combining said first and said second portions of said cells with an efflux media, said efflux media comprising an ABCA1 acceptor, and measuring the amount of substrate that associates with said ABCA1 acceptor in each of said portions of said cells.

In yet another preferred embodiment of the first aspect, a positive control composition is added to a third portion of said cells, said positive control composition being essentially identical to said control composition except that said positive control composition comprises an ABCA1 agonist, a negative control composition is added to a fourth portion of said cells, said negative control composition being essentially identical to said control composition except that said negative control composition comprises an ABCA1 antagonist, and wherein the levels of efflux of substrate from said third and said fourth portions of said cells are compared to the levels of efflux of substrate from said first and said second portions of said cells In a second aspect, the present invention relates to a method of determining the ability of a test compound to affect the activity of ABCA1 protein, said method comprising the steps of introducing labeled anions into ABCA1-expressing cells, adding a test composition comprising said test compound to a first portion of said cells, and adding a control composition to a second portion of said cells, wherein said control composition is essentially identical to said test composition except that said control composition does not include said test compound, and comparing the level of efflux of anions from said first portion of said cells to the level of efflux of anions from said second portion of said cells, wherein a change in the level of efflux indicates that said test compound affects the activity of the ABCA1 protein.

In a third aspect, the present invention relates to a method of determining the ability of a test compound to affect the transcription of ABCA1 mRNA, said method comprising the steps of adding a test composition comprising said test compound to a first portion of ABCA1-expressing cells, and adding a control composition to a second portion of said cells, wherein said control composition is essentially identical to said test composition except that said control composition does not include said test compound, and comparing the amount of ABCA1 mRNA from said first portion of said cells to the amount of ABCA1 mRNA from said second portion of said cells, wherein a change in the amount of ABCA1 mRNA indicates that said test compound affects the transcription of ABCA1 mRNA.

In a fourth aspect, the present invention relates to a method of determining the ability of a test compound to affect the expression of ABCA1 protein, said method comprising the steps of adding a test composition comprising said test compound to a first portion of ABCA1-expressing cells, and adding a control composition to a second portion of said cells, wherein said control composition is essentially identical to said test composition except that said control composition does not include said test compound, and comparing the amount of ABCA1 protein from said first portion of said cells to the amount of ABCA1 protein from said second portion of said cells, wherein a change in the amount of ABCA1 protein indicates that said test compound affects the expression of the ABCA1 protein.

DETAILED DESCRIPTION OF THE INVENTION

Because ABCA1 has been shown to be linked with the transport of cholesterol and phospholipids across the cellular membrane, it is believed that the discovery of compounds that modulate the activity of ABCA1 will lead to new drug treatments for atherosclerosis and other cardiovascular diseases. As such, the present invention, that provides methods for measuring the activity levels of ABCA1 protein, will be especially useful for the discovery of these compounds.

DEFINITIONS

ABCA1: This refers to the protein known as ABCA1 in the literature, and may also be used to refer to the gene encoding this protein. Specifically, this term refers to the protein encoded by the gene cloned by Chimini, as discussed in Luciani et al. (44). In addition to ABCA1 having the specific DNA or amino acid sequence as disclosed therein, the use of the term herein includes naturally occurring variants, as well as man-made variants, thereof. It is also worth noting that this protein and its gene have also been refered to as ABC1. In the present application, a mention of either ABC1 or ABCA1 is intended to refer to the same protein or gene, and ABC and ABCA are intended to refer to the same family of proteins or genes.

ABCA1-expressing cells: Any cell type that naturally expresses ABCA1, or which has been genetically engineered to express ABCA1, including both prokaryotic and eukaryotic cell types.

ABCA1 acceptor: Any compound that is capable of accepting a substrate from ABCA1. Known ABCA1 acceptors include apo A1, apo-AIV, apo-CI, apo-CII, apo-CIII, apo-E, apo-E2, apo-E3, apo-E4, and alpha-helix peptides.

ABCA1 agonist: Any compound that is capable of increasing the activity level of ABCA1 in an ABCA1-expressing cell, whether this increase occurs through increasing the transcription, translation, or stability of ABCA1 mRNA, by modulating the activity of the ABCA1 protein directly, or by any other means that results in an increase of ABCA1 activity (as opposed to a compound that is not ABCA1, but which is capable of carrying out one or more ABCA1-like activities on its own). Known ABCA1 agonists include cAMP, cAMP analogs (e.g., cpt-cAMP), vanadate, protein kinase A, okadaic acid, prostaglandins, oxysterols, and PDE inhibitors.

ABCA1 antagonist: Any compound that is capable of decreasing the activity level of ABCA1 in an ABCA1-expressing cell, whether this decrease occurs through decreasing the transcription, translation, or stability of ABCA1 mRNA, by preventing the movement of ABCA1 protein to the cellular membrane, by modulating the activity of the ABCA1 protein directly, or by any other means that results in a decrease of ABCA1 activity. Known ABCA1 antagonists include glibenclamide, sulfobromophthalein, flufenamic acid, diphenylamine-2-carboxylic acid, DIDS, bumetianide, and furosemide.

Control composition: A composition that does not contain any compounds that are known to affect ABCA1 activity or expression, other than by maintaining the general good health of the cells in contact with the control composition.

Efflux media: A composition that contains at least one ABCA1 acceptor, wherein the efflux media is capable of supporting active transport of a substrate from a cell, mediated by ABCA1, to the ABCA1 acceptor.

Negative control composition: A composition that contains at least one known ABCA1 antagonist.

Positive control composition: A composition that contains at least one known ABCA1 agonist.

Substrate: As used herein, this term refers to any compound that is specifically and actively transported across a membrane by the ATP-powered activity of ABCA1 protein.

Test compound: A compound that is to be assayed for its ability to act as an ABCA1 agonist or antagonist, but which is not yet known to have either property.

Test composition: A composition that includes a test compound.

Practice of the assay methods disclosed and claimed herein requires the use of ABCA1-expressing cells. ABCA1 is known to be expressed in a wide variety of cells, from all types of higher organisms. In addition, cells that do not naturally express ABCA1, particularly non-mammalian cells such as bacteria or insect cells, may be engineered to produce functional ABCA1. Any of these cells might be useful in the present invention, although certain cell types are presently preferred. Useful properties for cells to be used in the present invention include the expression of functional ABCA1, the ability to grow readily in commercially-available medium, and the ability to adhere to commonly used substrates for cell culture.

Cells that have some or all of these properties, and that are known to be useful in the present invention include monocytes, macrophages, endothelial cells, fibroblasts, and hepatocytes. Presently preferred is the mouse macrophage cell line J774 and the human macrophage cell line THP.1.

In some cases, it will be possible to perform the assay using the same medium in which the cells are maintained and grown. Most often, it will be preferred to transfer the cells to a special medium prior to performing the present assay, in order to prepare the cells and/or provide the cells with labeled substrate. This medium may consist of standard cell culture medium to which has been added a known labeled substrate of ABCA1. In some cases, the composition of the medium may be modified to decrease the concentration of unlabeled substrate. In some cases, a labeled substrate may be provided in the regular growth and maintenance media of the cells.

Once the cells are ready to be used in the present assay, a test composition or a control composition is added to the cells. These compositions, in addition to any test or control compounds that may be therein, preferably include standard cell-culture medium and other additions, such as a serum or serum substitute, to maintain the health and overall responsiveness of the cells.

Several substrates can be used for detection of ABCA1 activity. These include lipids, cholesterol, and phospholipids, as well as anions such as iodide. For the purpose of identifying agents with potential for increasing HDL levels, cholesterol and phospholipids are the presently preferred substrates.

For the purpose of assaying ABCA1 activity, the appropriate substrate may be labeled by a variety of means, including by any radioisotope, such as tritium or carbon-14, deuterium, a fluorescent tag, luminescent tag, or the like. Depending on the instrumentation at hand, any labeling technique listed above would be useful. Radioisotopes are presently preferred.

To monitor the integrity of the assay, a variety of positive controls, which have been shown to increase ABCA1 activity, are preferably used. These include cAMP, cAMP analogs, vanadate, protein kinase A, prostaglandin E1, or the protein phosphatase inhibitor, okadaic acid. In addition, the activity of ABCA1 may be increased by increasing the levels of cholesterol or oxysterols in cells, such as by incubation of macrophage or macrophage-derived cell lines with acetylated LDL. Among these, the presently preferred method is the direct addition to the culture medium of a known agonist, most preferably cAMP or an active analog thereof.

A variety of negative controls can be used in an assay of ABCA1 activity. These include the chloride channel blockers DIDS, flufenamic acid, and diphenylamine-2-carboxylic acid. Also, ABCA1 activity can be decreased with the prostaglandin transporter inhibitor sulfobromophthalein, and the sulfonylurea compound glibenclamide. Likewise, any inhibitor of protein kinase A may be used. Most useful may be those which block ABCA1 activity to a significant extent, such as DIDS.

When using lipids, such as cholesterol or phospholipids as substrates, the use of an acceptor to solubilize the lipid substrate from the cellular membrane is advantageous. Such acceptors include a variety of apoproteins, such as apo-AI, apo-AII, apo-AIV, apo-CI, apo-CII, apo-CIII, apo-E, apo-E2, apo-E3, or apo-E4, as well as synthetic amphipathic peptides representing the alpha-helical domains of apoproteins. The most preferred are those which may be most easily attainable, either commercially or by preparation in the lab, such as apo-AI. In the case where an acceptor is used to remove an ABCA1 substrate from a cell membrane, the association of the substrate with the acceptor can be quantified by measuring the amount of labeled substrate in the medium, by determining the level of radiolabel, fluorescence, luminescence etc., depending on the method used to label the substrate.

In the case where the analysis of ABCA1 expression is required, total RNA may be isolated (e.g., by the method according to Chomczynski et al., *N. Anal. Biochem.*, 162:156 (1987)) and ABCA1 mRNA levels determined by standard techniques such as Northern blotting, slot blot hybridization, or Ribonuclease protection assays using ABCA1 specific mRNA probes.

The detection and quantitation of ABCA1 protein may be carried out using standard techniques, preferably those that utilize antibodies specific for ABCA1. Among these, Western blotting, ELISA, dot/slot blots, and radioimmunoassays are presently preferred.

EXAMPLES

Cell Culture

Stock cultures of J774 mouse macrophage cell line were grown in RPMI 1640 supplemented with 10% FBS and 50 µg/ml gentamicin at 37° C. in a humidified atmosphere containing 95% air and 5% $CO_2$.

Lipid Radiolabeling

Cells were seeded in 96 wells (96-well plate, 0.15 ml/well) using 50,000 to 100,000 cells per well and grown in RPMI 1640–10% FBS and 0.5% gentamicin at 37° C. for 72 hours to achieve 80–90% confluence. Radiolabeled cholesterol ([1,2-$^3$H] cholesterol, New England Nuclear) was added to the cells by adding a tracer amount (1–5 µCi/well in a final concentration of 0.1% ethanol) to FBS, which was then diluted to a final concentration of 1% in RPMI. An acyl-CoA cholesterol acyltransferase (ACAT) inhibitor (decanamide, 2-(hexylthio)-N-[6-methyl-2,4-bis (methylthio)-3-pyridinyl]-,(2S)-(9Cl) at 2 µg/ml) was added to the labeling medium. At this concentration, ACAT activity was completely inhibited, ensuring that all of the radiolabeled cholesterol is present as free cholesterol. Cells were grown in the presence of the radiolabel for two additional days to obtain confluent monolayers. For experiments where cells are enriched in free cholesterol, acetylated LDL (100 µg of protein/ml) was included in the labeling mixture. Following the labeling period, cells were extensively washed using MEM-Hepes medium supplemented with 0.5% gentamicin, and incubated with either cpt-cAMP (positive control) at 0.3 mM or test compounds (varying concentrations may be used, although 5 µm was selected for the present experiment) for an additional 16 hours.

Assay of Cellular Cholesterol Efflux

At the end of the pretreatment period with cpt-cAMP or test compounds, cells were extensively washed with MEM-Hepes medium containing gentamicin and incubated in RPMI 1640 medium containing the cholesterol acceptor apo-AI at a final concentration of 20 µg/ml. Parallel monolayers of control or treated cells were also incubated with acceptor-free medium to determine background, non-acceptor mediated cholesterol efflux. Cellular cholesterol efflux was quantified by measuring the release of cellular [$^3$H]-cholesterol into the medium as a function of time. An aliquot of the incubation medium was filtered using a 0.45 micron Millipore multiscreen plate to remove any floating cells and then counted using a Wallac Microbeta Counter (Perkin-Elmer Life Sciences, Turku, Finland).

The amount of radiolabeled cholesterol released from the cells (% efflux) is determined by the amount of radioactivity present in the incubation medium divided by the radioactivity at time zero ($T_0$). Radtio activty at time zero is calculated as the amount of radioactivity in the cells as determined by isopropanol extraction at the end of the treatment time.

Some results of initial test compounds are presented below in Table 1.

TABLE 1

| Compound | Concentration | % of control | % of control mRNA |
|---|---|---|---|
| cpt-cAMP | 0.3 mM | 425 | 1600 |
| 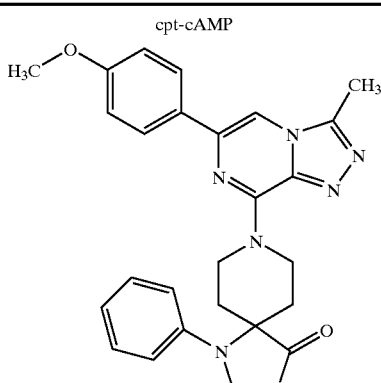 | 5 µM | 101 | |
| 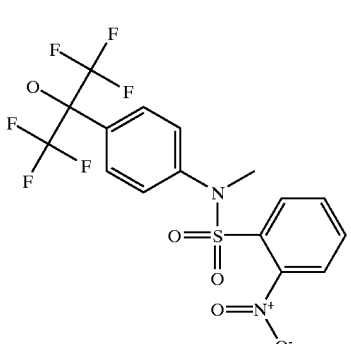 | 5 µM | 185 | 160 |

TABLE 1-continued

| Compound | Concentration | % of control | % of control mRNA |
|---|---|---|---|
| (structure) | 5 μM | 177 | 680 |
| Prostaglandin E1 | 1 μM | 210 | 1420 |
| (structure) | 5 μM | 106 | |
| (structure) | 5 μM | 94 | |
| (structure) | 5 μM | 111 | |

TABLE 1-continued

| Compound | Concentration | % of control | % of control mRNA |
|---|---|---|---|
| [structure] | 5 μM | 82 | |
| [structure] | 5 μM | 95 | |
| [structure] | 5 μM | 102 | |
| [structure] | 5 μM | 109 | |
| Efflux media | | 100 | 100 |

References

1. Higgins, *Annu. Rev. Cell Biol.*, 8:67–113 (1992)
2. Ames et al., *FASEB J.*, 6:2660–66 (1992)
3. Higgins, *Cell*, 82:693–96 (1995)
4. Gottesman et al., *Annu. Rev. Biochem.*, 62:385–428 (1992)
5. Thomas et al., *Science*, 268:426–29 (1995)
6. Riordan et al., *Science*, 245:1066–73 (1989)
7. Hanrahan et al., in *Ion Channels and Genetic Diseases* (Dawson, D. C. & Frizzell, R. A., Eds.) Vol. 50, pp. 125–137, Society of General Physiologists Symposium Series, Rockefeller University Press, New York (1995)
8. Sarkadi et al., *J. Biol. Chem.*, 267:4854–58 (1992)
9. Shapiro et al., *J. Biol. Chem.*, 269:3745–54 (1994)
10. Ko et al., *J. Biol. Chem.*, 270:22093–96 (1995)
11. Doige et al., *Biochim. Biophys. Acta*, 1109:149–60 (1992)
12. Müller et al., *J. Biol. Chem.*, 271:1877–83 (1996)
13. Beaudet et al., *J. Biol. Chem.*, 270:17159–70 (1995)
14. Baukrowitz et al., *Neuron*, 12:473–82 (1994)
15. Carson et al., *J. Biol. Chem.*, 270:1711–17 (1995)
16. Gunderson et al., *Cell*, 82:231–39 (1995)
17. Smit et al., *PNAS*, 90:9963–67 (1993)
18. Picciotto et al., *J. Biol. Chem.* 267:12742–52 (1992)
19. Gill et al., *Cell*, 71:23–32 (1992)
20. Hardy et al., *EMBO J.*, 14:68–75 (1995)
21. Walker et al., *EMBO J.*, 1:945–51 (1982)
22. Saraste et al., *Trends Biochem. Sci.*, 15:430–34 (1990)
23. Miler et al., *Lancet*, 1:965–68 (1977)
24. Keys, *Lancet*, 2:603–06 (1980)
25. Shaefer, *Arteriosclerosis*, 4:303–22 (1984)
26. Glomset, *J. Lipid Res.*, 9:155–67 (1968)
27. Fielding et al., *J. Lipid Res.*, 38:1503–21 (1997)
28. Oram et al., *J. Lipid Res.*, 37:2743–91 (1996)
29. Mendez, *J. Lipid Res.*, 38:1807–21 (1997)
30. Remaley et al., *Arterioscler. Thromb. Vasc. Biol.*, 17:1813–21 (1997)
31. Mendez et al., *J. Lipid Res.*, 37:2510–24 (1996)
32. Fredrickson, *J. Clin. Invest*, 43:228–36 (1964)
33. Assmann et al., in *The Metabolic Basis of Inherited Disease*, pp. 2053–72, Scriver et al., Eds., McGraw-Hill, New York, N.Y. (1995)
34. Serfaty-Lacrosniere et al., *Atherosclerosis*, 107:85–98 (1994)
35. Francis et al., *J. Clin. Invest*, 96:78–87 (1995)
36. Rogler et al., *Arterioscler. Thromb. Vasc. Biol.*, 15:683–90 (1995)
37. Walter et al., *Biochem. Biophys. Res. Comm.*, 205:850–56 (1994)
38. Horowitz et al., *J. Clin. Invest.*, 91:1743–52 (1993)
39. Rothblat et al., *J. Lipid Res.*, 40:781–96 (1999)
40. Lawn et al., *J. Clin. Invest*, 104(8):R25–R31 (1999)
41. Brooks-Wilson et al., *Nature Genetics*, 22:336–45 (1999)
42. Bodzioch et al., *Nature Genetics*, 22:347–51 (1999)
43. Rust et al., *Nature Genetics*, 22:352–55 (1999)
44. Luciani et al., *Genomics*, 21:150–59 (1994)
45. Becq et al., *J. Biol. Chem.*, 272:2695–99 (1997)
46. Langmann et al., *Biochem. Biophys. Res. Comm.*, 257:29–33 (1999)
47. Langmann et al., *Biochem. Biophys. Res. Comm.*, 258:73–76 (1999)
48. Young et al., *Nature Genetics*, 22:316–18 (1999)

What is claimed is:

1. A method of determining the ability of a test compound to affect the activity of ABCA1 protein, said method comprising the steps of:
   a) introducing labeled substrate into ABCA1-expressing cells;
   b) adding a test composition comprising said test compound to a first portion of said cells, and adding a control composition to a second portion of said cells, wherein said control composition is essentially identical to said test composition except that said control composition does not include said test compound;
   c) measuring the level of efflux of substrate from each portion of said cells by separately combining said first and said second portions of said cells with an efflux media, said efflux media comprising an ABCA1 acceptor, and measuring the amount of substrate that associates with said ABCA1 acceptor in each of said portions of said cells; and
   d) comparing the level of efflux of substrate from said first portion of said cells to the level of efflux of substrate from said second portion of said cells, wherein a change in the level of efflux indicates that said test compound affects the activity of the ABCA1 protein.

2. The method of claim 1, wherein said substrate is cholesterol or a phospholipid.

3. The method of claim 1, wherein said cells are mouse macrophage J774 cells, monocytes, macrophages, hepatocytes, endothelial cells, fibroblasts, or enterocytes.

4. The method of claim 1 wherein said substrate is labeled with tritium, carbon-14, deuterium, a fluorescent tag, or a luminescent tag.

5. The method of claim 1 wherein a positive control composition is added to a third portion of said cells, said positive control composition being essentially identical to said control composition except that said positive control composition comprises an ABCA1 agonist, and wherein the level of efflux of substrate from said third portion of said cells is compared to the levels of efflux of substrate from said first and said second portions of said cells.

6. The method of claim 5 wherein said ABCA1 agonist is cAMP, cpt-cAMP, vanadate, protein kinase A, okadaic acid, prostaglandin E1, or PDE inhibitors.

7. The method of claim 1 wherein a negative control composition is added to a third portion of said cells, said negative control composition being essentially identical to said control composition except that said negative control composition comprises an ABCA1 antagonist, and wherein the level of efflux of substrate from said third portion of said cells is compared to the levels of efflux of substrate from said first and said second portions of said cells.

8. The method of claim 7 wherein said ABCA1 antagonist is glibenclamide, sulfobromophthalein, flufenamic acid, diphenylamine-2-carboxylic acid, DIDS, bumetianide, or furosemide.

9. The method of claim 1 wherein said ABCA1 acceptor is apo-AI, apo-AIV, apo-CI, apo-CII, apo-CIII, apo-E, apo-E2, apo-E3, apo-E4, or a synthetic amphipathic peptide representing the alpha-helical domain of an apoprotein.

10. The method of claim 9 wherein said ABCA1 acceptor is apo-AI.

11. The method of claim 1 wherein the amount of substrate that associates with an acceptor for ABCA1 is measured by determining the amount of labeled substrate that appears in the medium of the cells.

12. The method of claim 1 wherein a positive control composition is added to a third portion of said cells, said positive control composition being essentially identical to said control composition except that said positive control composition comprises an ABCA1 agonist, a negative control composition is added to a fourth portion of said cells, said negative control composition being essentially identical to said control composition except that said negative control composition comprises an ABCA1 antagonist, and wherein the levels of efflux of substrate from said third and said fourth portions of said cells are compared to the levels of efflux of substrate from said first and said second portions of said cells.

13. A method of determining the ability of a test compound to affect the activity of ABCA1 protein, said method comprising the steps of:
   a) introducing labeled anions into ABCA1-expressing cells;
   b) adding a test composition comprising said test compound to a first portion of said cells, and adding a control composition to a second portion of said cells, wherein said control composition is essentially identical to said test composition except that said control composition does not include said test compound; and
   c) comparing the level of efflux of anions from said first portion of said cells to the level of efflux of anions from said second portion of said cells, wherein a change in the level of efflux indicates that said test compound affects the activity of the ABCA1 protein.

14. A method of determining the ability of a test compound to affect the transcription of ABCA1 mRNA, said method comprising the steps of:
   a) adding a test composition comprising said test compound to a first portion of ABCA1-expressing cells, and adding a control composition to a second portion of said cells, wherein said control composition is essentially identical to said test composition except that said control composition does not include said test compound; and
   b) comparing the amount of ABCA1 mRNA from said first portion of said cells to the amount of ABCA1 mRNA from said second portion of said cells, wherein a change in the amount of ABCA1 mRNA indicates that said test compound affects the transcription of ABCA1 mRNA.

15. A method of determining the ability of a test compound to affect the expression of ABCA1 protein, said method comprising the steps of:
   a) adding a test composition comprising said test compound to a first portion of ABCA1-expressing cells, and adding a control composition to a second portion of said cells, wherein said control composition is essentially identical to said test composition except that said control composition does not include said test compound; and
   b) comparing the amount of ABCA1 protein from said first portion of said cells to the amount of ABCA1 protein from said second portion of said cells, wherein a change in the amount of ABCA1 protein indicates that said test compound affects the expression of the ABCA1 protein.

* * * * *

(12) EX PARTE REEXAMINATION CERTIFICATE (5704th)
United States Patent
Bamberger et al.

(10) Number: US 6,555,323 C1
(45) Certificate Issued: Mar. 13, 2007

(54) ASSAY FOR ABCA1

(75) Inventors: Mark J. Bamberger, South Glastonbury, CT (US); Omar L. Francone, East Lyme, CT (US)

(73) Assignees: Pfizer Inc., New York, NY (US); Pfizer Products Inc., Groton, CT (US)

Reexamination Request:
No. 90/007,595, Jun. 17, 2005

Reexamination Certificate for:
Patent No.: 6,555,323
Issued: Apr. 29, 2003
Appl. No.: 09/761,890
Filed: Jan. 17, 2001

Related U.S. Application Data

(60) Provisional application No. 60/180,943, filed on Feb. 8, 2000.

(51) Int. Cl.
*G01N 33/53* (2006.01)

(52) U.S. Cl. .................. 435/7.1; 435/7.2; 435/7.21; 435/4; 435/6

(58) Field of Classification Search ................... None
See application file for complete search history.

(56) References Cited

U.S. PATENT DOCUMENTS 6,617,122 B1   9/2003  Hayden et al.

FOREIGN PATENT DOCUMENTS

| WO | WO 97/17359 | 5/1997 |
| WO | WO 98/03548 | 1/1998 |
| WO | WO 98/24818 | 6/1998 |

OTHER PUBLICATIONS

Becq et al., ABC1, an ATP Binding Cassette Transporter Required for Phagocytosis of Apoptotic Cells, Generates a Regulated Anion Flax after Expression in *Xenopus laevis* Oocytes, *J. Biol. Chem.* 272(5): 2695–2699 (1997).

Broach et al., High–throughput screening for drug discovery, *Nature* 384 Suppl.:14–16 (1996).

Burbaum et al., New Technologies for high–throughput screening, *Curr. Opin Chem. Biol.* 1: 72–78 (1997).

Marcil et al., Cellular Cholesterol Transport and Efflux in Fibroblasts are Abnormal in Subjects with Familial HDL Deficiency, *Arterioscler. Throm. Vasc. Biol.* 19(1): 159–169 (Jan. 1999).

Mendez, "Monensin and Brefeldin A Inhibit High Density Lipoprotein–mediated Cholesterol Efflux from Cholesterol–enriched Cells," *J. Biol. Chem.* 270: 5891–5900 (1995).

*Primary Examiner*—Padmashri Ponnaluri

(57) ABSTRACT

This invention relates to novel methods of measuring the activity and/or levels of ABCA1 protein, including the use of acceptors of ABCA1 substrates, as well as methods involving the measurement of ABCA1 mRNA and protein levels.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–15 are cancelled.

\* \* \* \* \*